United States Patent
Kasper

(10) Patent No.: US 9,993,371 B2
(45) Date of Patent: Jun. 12, 2018

(54) DEVICE FOR ABSORPTION AND CONTROLLED DISCHARGE OF LIQUID EXCRETIONS

(71) Applicant: Werner Kasper, Koenigstein (DE)

(72) Inventor: Werner Kasper, Koenigstein (DE)

( * ) Notice: Subject to any disclaimer, the term of this patent is extended or adjusted under 35 U.S.C. 154(b) by 407 days.

(21) Appl. No.: 14/736,678

(22) Filed: Jun. 11, 2015

(65) Prior Publication Data
US 2016/0361208 A1 Dec. 15, 2016

(51) Int. Cl.
A61F 13/20 (2006.01)
A61F 5/455 (2006.01)
A61F 13/26 (2006.01)

(52) U.S. Cl.
CPC ...... *A61F 13/2022* (2013.01); *A61F 13/2002* (2013.01); *A61F 13/204* (2013.01); *A61F 13/2042* (2013.01); *A61F 13/26* (2013.01); *A61F 5/4553* (2013.01)

(58) Field of Classification Search
CPC .............. A61F 13/2042; A61F 13/2045; A61F 5/4553; A61F 13/2002; A61F 13/2022; A61F 13/204; A61F 13/26
USPC ........................................ 604/11–18, 358.17
See application file for complete search history.

(56) References Cited

U.S. PATENT DOCUMENTS

| | | | | |
|---|---|---|---|---|
| 4,141,360 A | * | 2/1979 | Lasswell | A61B 17/42 604/181 |
| 5,247,941 A | * | 9/1993 | Andresen | A61B 10/0045 600/575 |
| 5,542,914 A | * | 8/1996 | Van Iten | A61F 13/2051 604/11 |
| 6,096,047 A | * | 8/2000 | Smit | A61F 5/4553 600/208 |
| 8,690,847 B2 | * | 4/2014 | Norman | A61F 5/4553 604/317 |

FOREIGN PATENT DOCUMENTS

| | | |
|---|---|---|
| DE | 20 2009 008 893 U1 | 10/2009 |
| GB | 2 349 573 A | 11/2000 |
| WO | 2006033539 A | 3/2006 |
| WO | 2009126088 A1 | 10/2009 |
| WO | 2011051502 A1 | 5/2011 |

* cited by examiner

*Primary Examiner* — Lynne Anderson
(74) *Attorney, Agent, or Firm* — Fish IP Law, LLP

(57) ABSTRACT

The device (10) has a handle (16) fixed to an end of a shaft (14). The handle is provided for the insertion of a detachable collection container (12) into a vagina, for rotation of the collection container about its longitudinal axis within the vagina or for the removal of the collection container from the vagina. The handle is provided with a hole (24), which is connected with the hollow interior of the shaft or a ventilation tube to ensure the supply of air to prevent pressure differences during removal of the collection container from the vagina. An independent claim is included for a method for absorption and controlled discharge of liquid excretion from a vagina.

12 Claims, 5 Drawing Sheets

DEVICE FOR ABSORPTION AND CONTROLLED DISCHARGE OF LIQUID EXCRETIONS

FIELD OF THE INVENTION

The field of the invention relates to a device for absorption and controlled discharge of liquid excretions from a vagina.

BACKGROUND

Known devices for the collection of liquid excretions of a vagina are, for example, devices for the collection of menstrual liquid, which can be inserted in the vagina for a limited time period, placed there and removed again.

A known device of this type is described in DE 20 2009 008 893 U1. Here, for the collection of menstrual liquid an approximately cup- or funnel-shaped (open at the top) elastic shell is described, which can be inserted into the vagina or removed again by means of a handle integrally formed outwards in its longitudinal axis.

Another document (WO 06033539 A1) describes, for example, a "vessel of menstruation." Here, for example, a collection and discharge of liquid menstrual excretions occurs by means of an actively manageable device, which is inserted for this purpose for a limited time into the vagina and subsequently removed again.

The further document (GB 2 249 573 A) describes a method or a device for the collection of vaginal secretion or of menstruation liquid for diagnostic purposes. For this purpose an absorbent medium is positioned interlabially or intravaginally. The liquid is collected by the absorbent medium. Then the medium is removed, the collected liquid extracted from it and supplied to the medical diagnostics. For the intravaginal collection of liquid, the absorbent medium can also be placed in a housing with fluid intake openings before the insertion into the vagina. An unwanted outflow of vaginal liquid is prevented here by the use of the absorbent material in the interior of the collection container.

Document WO 2009/126088 A1 relates to a hygiene protective means, which is intended for placement in the vagina of a user. The hygiene protective means is characterized by a shell-like base body, which is narrowed from the center upwards and downwards. The base body is thereby provided with openings for a liquid intake at a designated part of its surface, whereby an outflow of liquid is prevented.

In document WO 2011/051502 A1 a device for the removal of liquid from a vagina is also described. The device consists preferably of a biologically inert, non-absorbent material. It has an elongated body (container) and a decoupling element. The device is inserted into the vagina and left in the vagina for a certain period of time. Vaginal liquid is thereby taken into the interior of the container through openings in the outer wall of the container. When required, the device is then pulled out of the vagina after a sufficient intake of liquid.

In particular, after a sexual act leakage of existing semen (ejaculate) from the vagina can occur over a longer time period. As a rule, soiling, for example of bed linen, underwear etc. occurs here. Additionally, in the case of women an uncomfortable feeling of incontinence frequently occurs, which is not or not sufficiently reduced or prevented by the use of hygiene products, such as panty liners or similar absorbent products.

However, essentially no known device discloses a possibility specifically for absorption and controlled (targeted) discharge of liquid excretions from the vagina, which were introduced into the vagina during a sexual act, for example, semen.

The problem addressed by the invention is to indicate a device, by means of which an absorption and controlled discharge of liquid excretions from a vagina is made possible.

SUMMARY OF THE INVENTION

This problem is solved by the invention with the features of the independent claim. Advantageous further developments of the invention are characterized in the sub-claims. The wording of all claims is incorporated into this description by reference. The invention also comprises all reasonable and in particular all mentioned combinations of independent and/or dependent claims.

A device for absorption and controlled discharge of liquid excretions from a vagina is proposed, which has a collection container for absorbing and collecting liquid excretions.

The collection container is designed as a hollow body with a longitudinal axis, which is closed by two ends.

The collection container thereby has a maximum outer diameter perpendicular to its longitudinal axis of 20 to 30 mm.

A large number of holes are introduced into the outer wall of the collection container, so that the liquid excretions can enter through these into the collection container.

The holes introduced into the outer wall of the collection container have a diameter of 0.8 mm to 1.5 mm, preferably of 1.0 mm.

Furthermore, a shaft exists, which is permanently connected to the collection container. The shaft or a ventilation tube thereby partially protrudes with a first (top) end through one of the ends of the collection container along the longitudinal axis of the collection container into the collection container.

A handle is fixed on the opposite end of the shaft.

By means of the handle an insertion of the collection container into the vagina as well as a rotation process of the collection container about its longitudinal axis can be executed within the vagina. By means of the handle the removal of the collection container from the vagina is also made possible.

A hole is introduced into the handle such that it is connected in a communicating manner to the hollow interior of the shaft or to the ventilation tube, in order to ensure an air supply when the collection container is removed from the vagina for the purpose of preventing any pressure differences from occurring.

The device makes it possible, in particular, to prevent an uncontrolled outflow of ejaculate from the vagina after a sexual act and thus also to prevent linen soiling, for example, of bed linen and/or underwear.

Through the existence of the shaft or tube protruding into the collection container it is prevented that liquid exits through the same at the handle.

Without the hole in the handle pressure differences could arise when the collection container is removed from (pulled out of) the vagina. In order to compensate for any pressure differences during insertion and removal of the device, air can flow through the hole in the handle into the device. Through the compensation for possible pressure differences, when removing the collection container from the vagina the occurrence of a negative pressure, which could cause an unwanted suction effect, is prevented.

In an advantageous design the collection container can be disassembled appropriately perpendicular to its longitudinal axis into an upper and a lower half shell in order to permit an emptying and cleaning of the collection container.

In the design of the device without the possibility of disassembling the collection container into two half shells this embodiment of the device can be conceived, for example, as a disposable product. The embodiment which can be disassembled, however, permits a rinsing out and cleaning of the device and thus a repeated usability.

It is advantageous if the device is designed from a material biologically compatible with the human body, preferably from plastic.

It is advantageous if the device has a total length of 100 to 150 mm, preferably of 130 mm.

The collection container has an outer diameter of 20 to 30 mm, preferably of 25 mm. Adapted to the human body, a length of the collection container of 70 to 100 mm, preferably of 85 mm is also advantageous.

It is advantageous if the shaft has an outer diameter of 5 to 15 mm, preferably of 8 to 12 mm, and has a length of 25 to 80 mm, wherein the shaft or the ventilation tube protrudes up to a length of 20 to 30 mm, preferably of 25 mm, into the collection container.

The holes introduced into the outer wall of the collection container have a diameter of 0.8 mm to 1.5 mm, preferably of 1.0 mm.

The hole diameter of the side holes in the collection container is selected here with regard to a capillary effect which occurs, and a certain surface tension of the mucous liquid (for example, sperm fluid) such that the introduced liquid itself closes up the collection container on the longitudinal sides or cannot exit again under the influence of gravity alone.

It is also advantageous, if holes introduced into the outer wall of the collection container are arranged with a spacing of 4 to 6 mm, preferably of 5 mm.

Such an arrangement and number of holes ensures a sufficient possibility of the liquid entering into the interior of the collection container.

A hole introduced into the handle with a diameter of 1 to 8 mm, preferably of 4 mm is advantageous. The dimensions of the hole are sufficient in order to ensure the required pressure compensation.

The handle can have both a spherical shape as well as the form of other geometrical or biological bodies. However, all alternative forms should thereby be selected such that no corners or edges exist.

In one advantageous design the handle can also be disassembled into an upper and a lower half shell. In this connection, the ventilation tube is connected to the lower half shell, wherein the ventilation tube penetrates the lower half shell, in order to connect to the surrounding air in a communicating manner It is also advantageous if the handle is designed as a screw cap, which can be screwed on the shaft. In this design, the ventilation tube is connected to the screw cap, wherein the ventilation tube penetrates the screw cap in order to be connected to the surrounding air in a communicating manner.

The method for absorption and controlled discharge of liquid excretions from a vagina by means of the above-described device is carried out in an advantageous manner as described below.

Initially, the collection container of the device is inserted into the vagina after a sexual act by means of the handle.

The collection container remains in the vagina with a retention time of several minutes, preferably of 2 to 5 minutes.

During the stay in the vagina a number of slight rotations of the collection container are carried out about its longitudinal axis by means of the handle. Thus, an entry of liquid, preferably of ejaculate present in the vagina after a sexual act, is effected into the collection container.

The entry of the liquid thereby occurs through the holes present in the outer wall of the collection container.

After expiration of the provided retention time of the collection container in the vagina the collection container is removed from the vagina by being pulled out by means of the handle.

After the removal of the collection container from the vagina the device can be disposed of.

If the device is designed so that the collection container can be disassembled into two half shells, then after removal from the vagina it is disassembled perpendicular to its longitudinal axis into the two half shells and the absorbed liquid is removed by means of rinsing out or cleaning, particularly with dear water.

After the rinsing out and cleaning the two half shells of the collection container are detachably joined together again.

The device can now be used once again after the rinsing out and the cleaning, wherein the above-described steps are repeated in the case of a reuse.

The collection container is formed in length and diameter such that it can be placed comfortably behind the vaginal entrance and does not slip out on its own in the resting position. The device stays there for a few minutes (for example, two minutes). The slight rotary movements of the collection container along its longitudinal axis by rotation of the handle accelerate the process of the entry of the liquid to be absorbed into the collection container.

Assisted by the pressure of the vagina wall on the collection container and by the rotary movements, the liquid (sperm and vaginal secretion) is passed through the existing holes into the collection container of the device.

The collection container can have both a cylindrical form with hemispherical end as well as the form of other geometrical or biological bodies. However, all alternative forms should thereby be selected so that no corners or edges exist.

The handling of the device (the insertion of the collection container into the vagina, the rotation within the vagina, the removal from the vagina) requires a design adapted to the body, which ensures that, in the case of all processes connected to a certain friction on body tissues, such as insertion, rotation or removal of the collection container, any possibility of injury to a user is excluded.

Other particulars and features result from the following description of preferred embodiments in connection with the subclaims. In this connection, the respective features can be realized alone or together in combination with one another.

BRIEF DESCRIPTION OF THE DRAWINGS

The embodiments are schematically represented in the figures. The same reference numerals in the individual figures identify the same or functionally similar elements corresponding to each other in terms of their functions. In detail.

DETAILED DESCRIPTION

Figure 1:
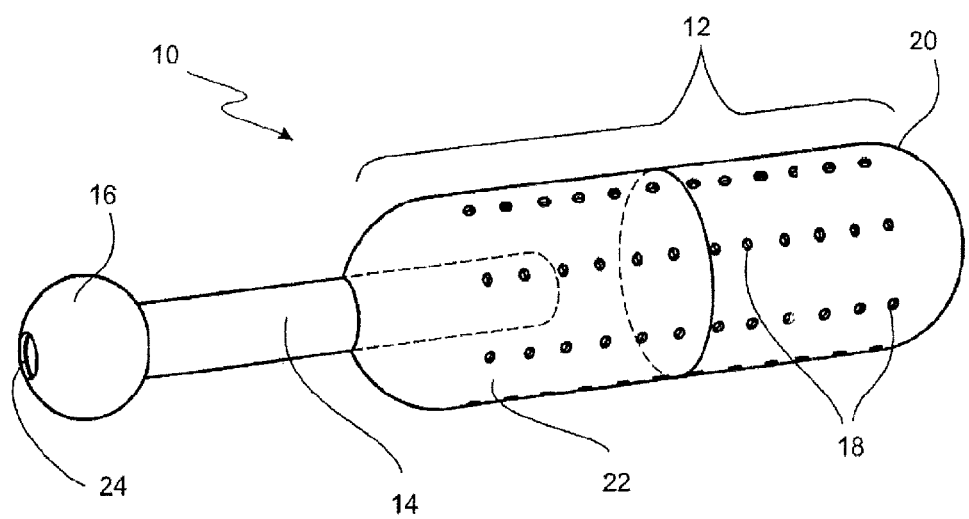
FIG. 1 shows a perspective full view (schematically) of a first embodiment of the device with a collection container which can be disassembled.

The first embodiment of the device 10 shown in FIG. 1 for absorption and controlled discharge of liquid excretions from a vagina consists of the following elements:
- a collection container 12,
- a tubular middle part (shaft) 14, and
- a spherical handle 16.

The device 10 preferably has a total length of 130 mm and is formed from a biologically compatible plastic.

The collection container 12 preferably has a diameter of 25 mm as well as a length of 85 mm. It consists advantageously of two half shells 20, 22, which are connected detachably to each other. A multiplicity of holes 18 arranged symmetrically to each other, in several rows, are introduced into the outer wall of the collection container 12. The holes 18 have a diameter of approx. 1.0 mm. The distance between the holes 18 is preferably 5 mm.

The tubular middle part 14 has an outer diameter of approx. 8 mm, and a total length of approx. 70 mm. On its upper end the middle part 14 is permanently connected to the collection container 12, wherein the middle part 14 thereby protrudes approximately 25 mm into the collection container 12.

On its lower end the shaft 14 is permanently connected to the handle 16.

A hole 24 with a diameter of approx. 4 mm is introduced into the handle 16 designed, for example, spherically.

After a sexual act the collection container 12 for absorbing and collecting liquid excretions from a vagina (preferably of semen) is inserted by means of the handle 16 into the vagina. There the collection container 12 stays a few minutes (preferably 2 minutes). Through the pressure of the vagina wall on the collection container 12 and, assisted by repeated slight rotation of the collection container 12 during the stay in the vagina by means of the handle 16 about the longitudinal axis of the device 10, an inflow or entry of the liquid to be discharged is effected through the holes 18 into the collection container 12. After absorbing the liquid the collection container 12 is removed from the vagina by means of the handle 16.

Air can flow into the device 10 through the hole 24 introduced into the handle, whereby possibly occurring pressure differences during the insertion or removal of the collection container 12 can be compensated for. At the same time the occurrence of a negative pressure during the removal of the device can be prevented.

By means of the shaft (tube) 14 reaching into the collection container 12 it can be prevented that the liquid exits at the spherical handle 16.

The collection container 12 can be opened after the removal from the vagina (can be disassembled perpendicular to its longitudinal axis into the two half shells 20, 22). Then the emptying (rinsing out) and cleaning occurs. After that the collection container 12 is joined together again and is prepared for a possible reuse.

Figure 2:
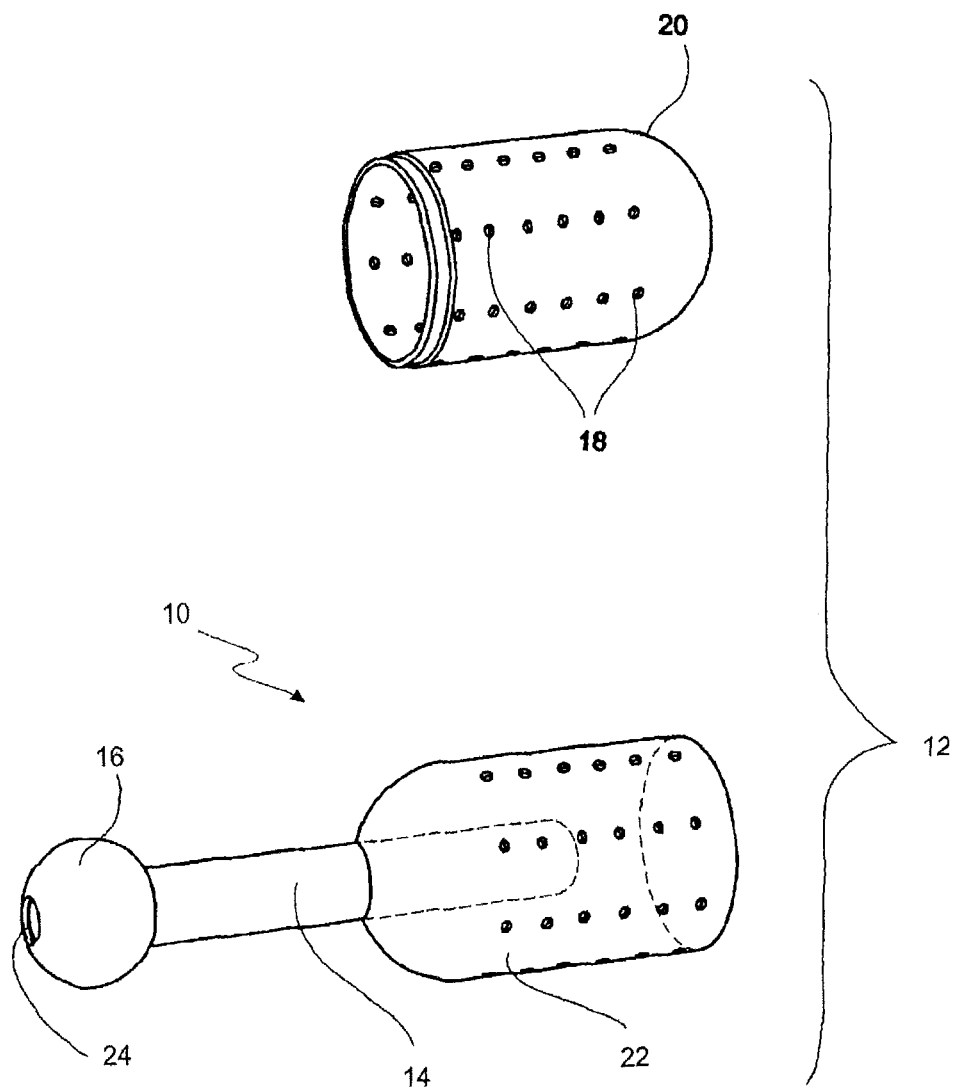
FIG. 2 shows a perspective view (schematically) of the device according to the first embodiment with the collection container disassembled into two half shells.

In FIG. 2 the device 10 is shown with opened collection container 12. The collection container 12 is here disassembled perpendicular to its longitudinal axis into the two half shells 20, 22, which after the rinsing out and cleaning with clear water are detachably reconnected to each other.

Otherwise, explanations given for FIG. 1 apply correspondingly to FIG. 2.

Figure 3:
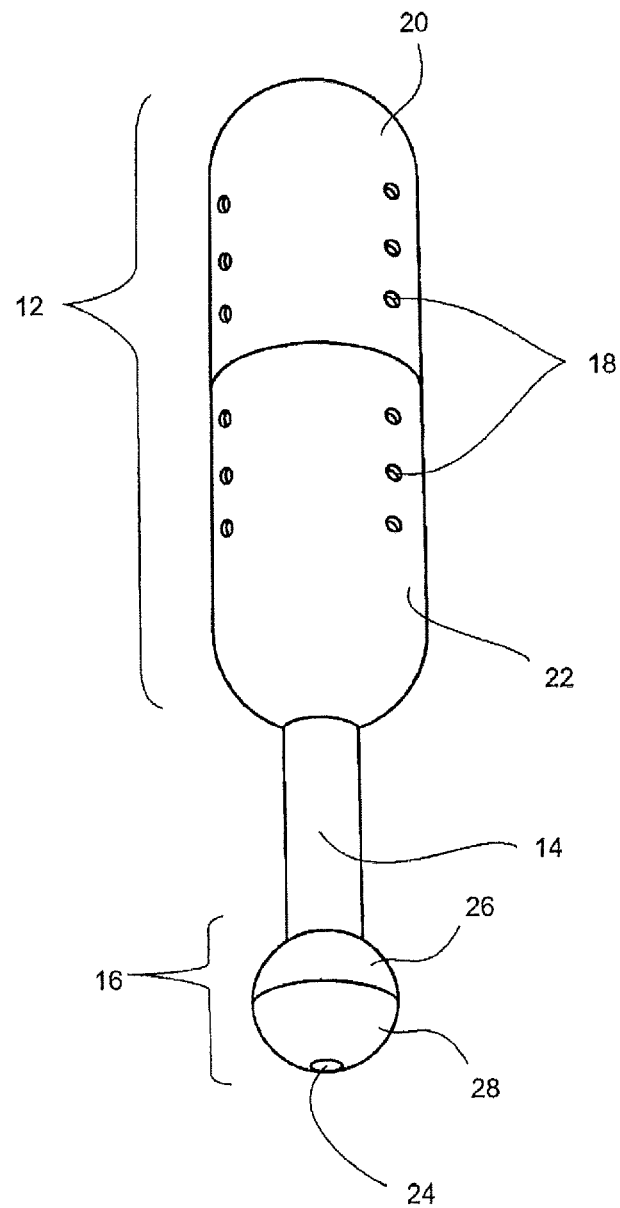
FIG. 3 shows a perspective full view (schematically) of a second embodiment of the device with a connection container which can be disassembled into two half sells and a handle which can be disassembled.
Figure 4:
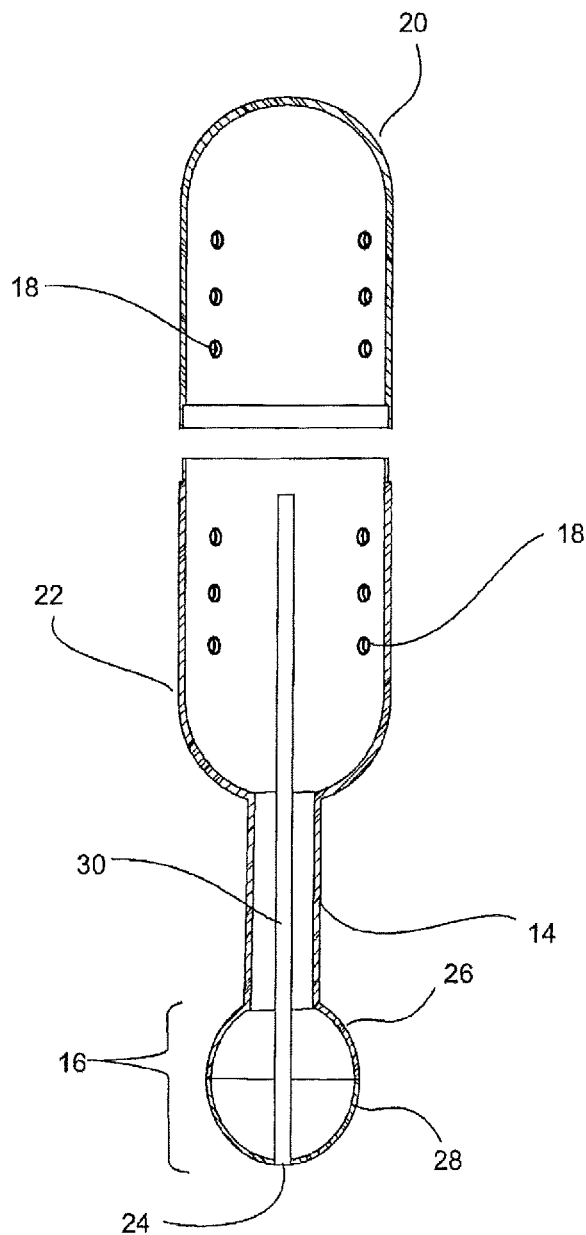
FIG. 4 shows a sectional view (longitudinal section; schematically) of the device according to the second embodiment.
Figure 5:
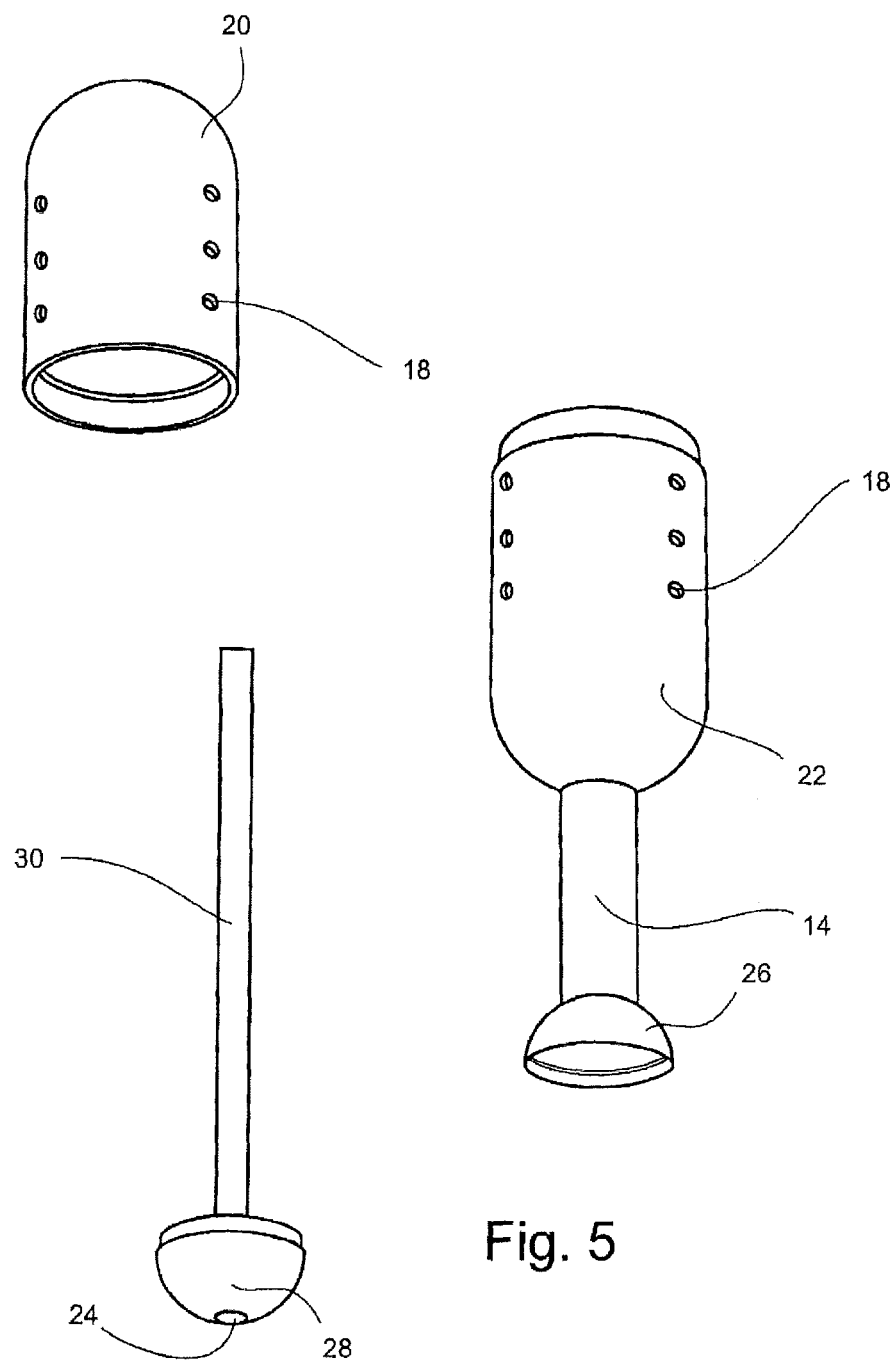
FIG. 5 shows a perspective view (schematically) of the device disassembled into the main elements according to the second embodiment.

The second embodiment of the device 10 shown in FIG. 3 to FIG. 5, compared to the first embodiment shown in FIG. 1 and FIG. 2 has some special features, which take into account the fact that the amount of liquid in the vagina can be significantly increased by introducing lubricants as well as by the use of vaginal suppositories for contraception. The problem in such a situation can consist in that in the vagina the amount of liquid to be discharged is increased such that the hydrostatic pressure which arises becomes greater than the surface tension of the liquid. This can have the consequence of an undesired dripping of the liquid out of the entry holes 18 of the device 10. Also, the surface tension can be reduced in addition by such means which counter the automatic shut-off effect.

The middle part (shaft) 14 as well as the handle 16 of the device 10 are in the case of the second embodiment also designed as hollow bodies. Among each other as well as with the collection container 12 they are permanently connected such that the liquid can reach unhindered from the collection container 12 up to the handle 16. Thus, the middle part 14 and handle 16 can serve as an additional liquid reservoir. The outer diameter (shaft diameter) of the middle part 14 is selected at approx. 2 mm larger than in the first embodiment, wherein the outer diameter (shaft diameter) is now approx. 10 mm.

The spherical handle 16 is in this embodiment of the device 10 designed so it can be disassembled, wherein a ventilation tube 30 is mounted on the outer, removable half part 28 of the handle 16. In the assembled state of the device 10 the ventilation tube 30 thereby leads on one side into the ventilation opening (hole) 24 of the removable half part 28 of the handle 16, while it protrudes with its opposite end into the lower collection container 22. In the case of the removal of the half part 28 of the handle 16 from the half part 26 the ventilation tube 30 mounted on it is simultaneously pulled out of the lower collection container 22 and the middle part (shaft) 14.

Through this modified design of the device 10 the leak-proof volume (in the perpendicular position of the device 10) increases compared to the first embodiment by more than the factor 3 to approx. 9.5 ml.

Otherwise, explanations given for FIG. 1 and FIG. 2 apply correspondingly to FIG. 3 to FIG. 5.

The invention claimed is:

1. A device for collection and controlled discharge of liquid excretions from a vagina having:
    a) a collection container for collecting the liquid excretions;
        a1) wherein the collection container comprises a hollow body with a longitudinal axis, which is closed by two ends;
        a2) wherein the collection container has a maximum outer diameter perpendicular to its longitudinal axis of 20 to 30 mm;

a3) wherein the collection container has an outer wall having a large number of holes, through which the liquid excretions can enter into the collection container;

a4) wherein each of the holes of the outer wall of the collection container have a diameter of 0.8 mm to 1.5 mm;

b) a shaft permanently connected to the collection container, b1) wherein a ventilating feature, selected from one of the shaft or a ventilation tube at least partially located within the shaft, comprises a cavity and a first end protruding partially into the collection container through one of the ends of the collection container along the longitudinal axis of the collection container;

b2) wherein on the end of the collection container opposite the shaft no holes are introduced into the outer wall;

c) a handle which is fixed on the opposite end of the shaft;

c1) wherein the handle permits an insertion of the collection container into the vagina or a rotation process of the collection container about its longitudinal axis within the vagina and/or a removal of the collection container from the vagina; and c2) wherein the handle comprises a hole in fluid communication with the cavity such that the handle is connected in a communicating manner to the cavity, in order to provide fluid communication between room air and the collection container for the purpose of preventing any pressure differences between room air and the collection container from occurring.

2. The device according to claim 1, characterized in -that the collection container can be disassembled perpendicular to its longitudinal axis into an upper and a lower half shell, in order to permit the emptying and cleaning of the collection container.

3. The device according to claim 1, characterized in that the device has a total length of 100 to 150 mm.

4. The device according to claim 1, characterized in that the collection container has a length of 70 to 100 mm.

5. The device according to claim 1, characterized in a) that the shaft has an outer diameter of 5 to 15 mm; and b) has a length of 25 to 80 mm.

6. The device according to claim 1, characterized in that the shaft or the ventilation tube protrudes into the collection container by a length of 20 to 30 mm.

7. The device according to claim 1, characterized in that the holes introduced into the outer wall of the collection container are ar-ranged with a spacing to each other of 4 to 6 mm.

8. The device according to claim 1, characterized in that the hole introduced into the handle has a diameter of 1 to 8 mm.

9. The device according to claim 1, wherein the ventilation feature is the ventilation tube at least partially located within the shaft, characterized in that the handle can be disassembled into an upper and a lower half shell; and that the ventilation tube is connected to the lower half shell; wherein the ventilation tube leads into the hole.

10. The device according to claim 1, wherein the ventilation feature is the ventilation tube at least partially located within the shaft, characterized in that the handle is designed as a screw cap, which can be screwed onto the shaft; wherein the ventilation tube leads into the hole.

11. A method for collection and controlled discharge of liquid excretions from a vagina by means of a device according to claim 1, having the following steps:

a) inserting the collection container of the device into the vagina by means of the handle;

b) the collection container remains in the vagina with a retention time of 2 to 5 minutes;

c) during the stay in the vagina carrying out a multiplicity of slight rotary movements of the collection container about the longitudinal axis of the device using the handle;

c1) wherein an entry of liquid excretions into the collection container is effected; and c2) wherein the entry of the liquid excretions occurs through the holes existing in the outer wall of the collection container;

d) after expiration of the retention time of the collection container in the vagina, removing the collection container from the vagina using the handle while introducing room air into the collection container utilizing a ventilation tube in fluid communication with the collection container and a hole of the handle.

12. The method according to claim 11, further comprising the steps of:

a) disassembling the collection container perpendicular to its longitudinal axis into a first half shell and a second half shells after the removal from the vagina;

b) removing the collected liquid is removed by rinsing out and cleaning the first half shell and the second half shells; and c) joining the first half shell and the second half shells of the collection container.

* * * * *